United States Patent [19]

Moran et al.

[11] 4,070,156
[45] Jan. 24, 1978

[54] REAGENT DISPENSING SYSTEM IN AN AUTOMATIC CHEMICAL ANALYZER

[75] Inventors: John J. Moran; Carl O. Gellenthin; James R. Eseke, all of Houston, Tex.

[73] Assignee: Hycel, Inc., Houston, Tex.

[21] Appl. No.: 725,238

[22] Filed: Sept. 21, 1976

[30] Foreign Application Priority Data

Mar. 17, 1976 United Kingdom ............... 10685/76
Mar. 17, 1976 United Kingdom ............... 10686/76

[51] Int. Cl.² .......................... G01N 1/14; G01N 1/18
[52] U.S. Cl. .................................... 23/253 R; 23/259; 73/425.6
[58] Field of Search ................. 23/253 R, 259, 230 R; 141/130; 73/425.6

[56] References Cited

U.S. PATENT DOCUMENTS

| | | | |
|---|---|---|---|
| 3,192,968 | 7/1965 | Baruch et al. | 23/259 X |
| 3,192,969 | 7/1965 | Baruch et al. | 23/259 X |
| 3,421,858 | 1/1969 | Quinn | 23/259 X |
| 3,572,130 | 3/1971 | Goldsmith | 23/259 X |
| 3,728,080 | 4/1973 | Moran | 23/253 X |

Primary Examiner—R.E. Serwin
Attorney, Agent, or Firm—Robert P. Cogan; Timothy L. Burgess

[57] ABSTRACT

In an automatic chemical analyzer, a reagent dispensing system is provided for delivering reagent from containers in a reagent compartment to reaction stations. A mounting block assembly is formed with a first bore therethrough for providing a reagent flow path whose direction of flow is regulated with check valves. A second bore normal to the first bore and communicating therewith is provided for receiving a piston having travel-limiting radial flange means formed at the end thereof remote from the first bore. A solenoid is mounted to the block having a plunger for activating the piston.

10 Claims, 2 Drawing Figures

REAGENT DISPENSING SYSTEM IN AN AUTOMATIC CHEMICAL ANALYZER

BACKGROUND OF THE INVENTION

This invention relates to automatic chemical testing apparatus, and more particularly to means for dispensing reagents therein.

The present invention relates to an improvement to the type of apparatus disclosed in U.S. Pat. No. 3,723,066 issued to John J. Moran on Mar. 27, 1973, assigned to the assignee herein, the disclosure of which is incorporated herein by reference. U.S. Pat. No. 3,728,079 issued to John J. Moran on Apr. 17, 1973, also commonly assigned which describes the operation of the type of chemical analyzer contemplated as the context for the present invention. The disclosure thereof is also incorporated herein by reference. In automatic chemical analyzer, samples to be analyzed, for example human serum, are added to reaction containers, reagents are combined therewith, and the reacted contents of the reaction container are analyzed for the present of a particular substance. It is necessary to dispense accurately a given amount of reagent to each sample container. Precision of amounts to be dispensed must be on the order of microliters. Another way in which pumping and dispensing systems in automatic chemical analyzers are distinguished from pumping and dispensing systems in general is that it is very important to have a limited amount of dead volume, i.e. volume remaining in pumping means after a pump stroke. It is necessary to rinse old reagent from pumping means upon a new period of analyzer usage commencing after a period of non-usage. Simply flushing water through reagent lines at the end of a period of usage is very expensive in terms of the skilled operator labor involved. Further, water remaining in hydraulic lines would dilute reagents being pumped at the beginning of a next period of usage. Further, the reagents in chemical analyzer systems tend to be quite expensive compared to fluids pumped by dispensing and pumping systems in general.

It is also desirable to provide for convenient, efficient mounting of pump means in a chemical analyzer and cooperation of pump means with fluid paths.

SUMMARY OF THE INVENTION

It is therefore an object of the present invention to provide in a chemical analyzer an improved apparatus for delivering accurately dispensed amounts of reagent from a source to a reaction station which is simple in construction and effective in operation.

It is a further object of the present invention to provide an apparatus of the type described in which efficient construction in provision of a piston cylinder for pumping, reagent path and pump mounting means is achieved.

Briefly stated, in accordance with the present invention there is provided a mounting block having at least one bore extending therethrough providing a reagent path with check valves in the vicinity of either end thereof. A second bore preferably normal thereto communicates with the first bore. A piston is provided in the second bore, and means are provided for limiting axial motion of the piston in either axial direction of its travel. Actuating means such as a solenoid are fixed to the block of operating the piston. A plurality of such assemblies may be formed in the same block. The inlet side of each first bore communicates with a source of reagent. The outlet side of each bore communicates with a means for delivering reagent to a reaction station.

BRIEF DESCRIPTION OF THE DRAWINGS

The means by which the foregoing objects and features of invention are achieved are pointed out with particularity in the claims forming the concluding portion of the specification. The invention, both as to its organization and manner of operation, may be further understood by reference to the following description taken in connection with the following drawings.

Of the drawings.

DESCRIPTION OF THE PREFERRED EMBODIMENT

Figure 1:
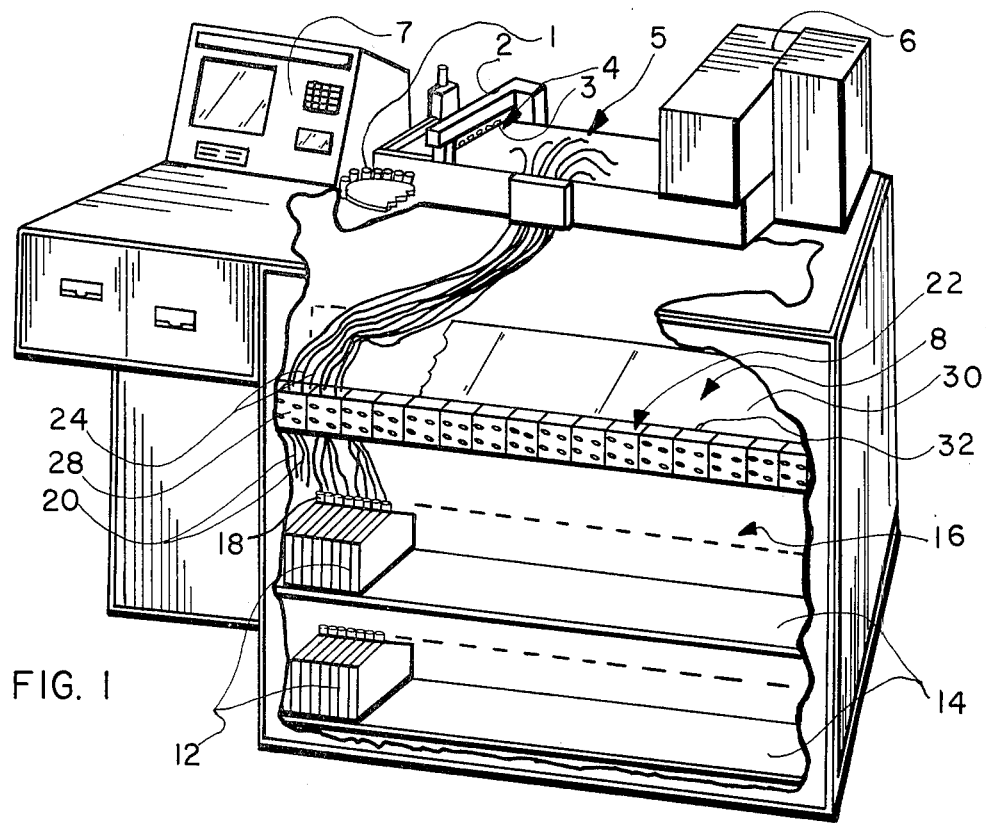
FIG. 1 is a view of a chemical analyzer employing the present invention.

Referring to FIG. 1, there is illustrated in axonometric form, a chemical testing apparatus of the type described in the above-cited Moran U.S. Pat. No. 3,728,079. A sample source 1 sequentially delivers successive samples to be tested, e.g. human serum, to sample dispensing means 2. The sample dispensing means 2 dispenses aliquots of serum to each of a number of reaction containers 3 in a reaction loop conveyor 4. Each row of reaction containers is indexed through a plurality of incubation and reagent dispensing stations 5. Reacted contents of reaction containers 3 are aspirated and analyzed in readout means 6. Keyboard and terminal means 7 replace the control and recording means of the above-cited Moran patents. Further reference may be had to those patents for description of the operation described above. A reagent supply system 8 is provided as further described below.

In illustrating the reagent supply system 8, a front panel of the chemical testing apparatus is partially broken away for facility of illustration. Reagent bottles 12 are each mounted on a shelf 14 in a housing 16. Each reagent bottle 14 has a cap 18 with a siphon line 20 extending therethrough for deliver of reagent from each of the respective bottles 14 to a reagent block assembly 22. The reagent block assembly 22 has a plurality of lines 24, each for completing a flow path for one reagent from the reagent assembly block 22, to a selected position in the reaction station 5.

The reagent dispensing block assembly 22 may be unitary, or may be comprised of a plurality of identical subassembly blocks 28. The reagent assembly block 22 and/or subassembly blocks 28 are mounted to a rear wall 30 of the housing 16 by means of standoffs 32. A plurality of pumps 36, each associated with one reagent system comprising one of the reagent bottles 12 and the lines 20 and 24 are mounted thereto. Since in the preferred embodiment each such reagent dispensing system may be identical, one such system is illustrated in FIG. 2, which is a cross-sectional view thereof.

Figure 2:
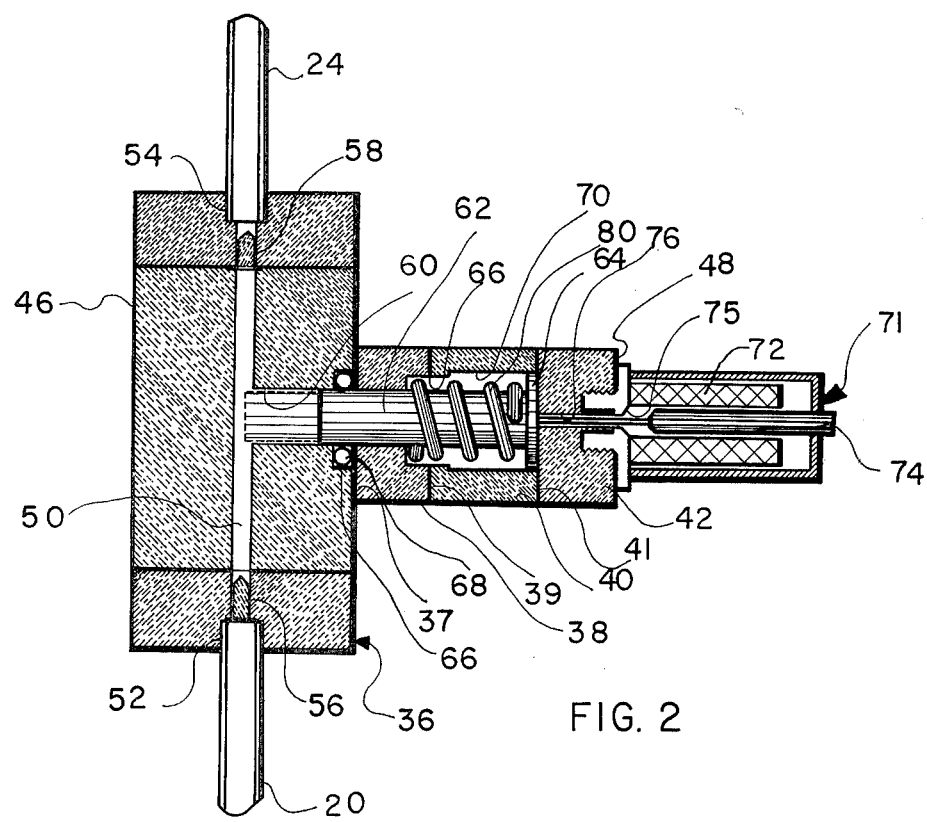
FIG. 2 is a cross sectional view of a pumping assembly constructed in accordance with the present invention incorporated therein.

In FIG. 2, it is seen that the reagent dispensing block 22 preferably comprises four sections 36, 38, 40 and 42 each extending in a lateral direction. The blocks 36 and 38 are joined at a trasverse interface 37. Specifications of directions are arbitrary, and are used herein for defining spatial relationships. The blocks 38 and 40 are joined at a transverse interface 39. Similarly, the blocks 40 and 42 have an interface 41. While it is not essential that four sections 36, 38, 40 and 42 be utilized, this construction facilitates ease of machining. The block 22 has a rear face 46 and a front face 48. It should be noted that terms such as front, transverse vertical and the like are arbitrary. They are used herein to define relative spatial relationships of the elements referred to for defining specifically the subject apparatus.

A vertical bore 50 providing a reagent flow path is formed in the section 36 of the block 22 preferably disposed toward the rear face 46 thereof. Seating means 52 receives an end of the line 20 in the bore 50. Seating means 52 links an opposite end of each bore 50 to the end of each line 24. An inlet check valve 56 and an outlet check valve 58 are also provided in each bore 50. Alternatively, the check valves 56 and 58 may be provided in the lines 20 and 24 respectively. The block 22 is preferably formed of acrylic material or of polyvinyl chloride (PVC).

A horizontal bore 60 communicates with the vertical bore 50 and extends forwardly thereof. The bore 60 receives a piston 62 having radially extending flange means 64 at a forward end thereof. A recess 66 coaxial with the bore 60 and extending rearwardly of the interface 37 retains fluid sealing means in the form of an O-ring 68 for cooperating with the piston 62 to provide a fluid seal between the rear and forward portions of the piston 62. A recess 65 coaxial with the bore 62 extends rearwardly of the interface 39. The radially extending flange 64 is received in a recess 70 coaxial with the bore 62 and extending rearwardly of the interface 41. The surface of the block 40 at the interface 41 and the rearward face of the recess 70 and the forward and rear surfaces of the radial flange 64 cooperate to define stop means for determining the axial travel of the piston 62 in the bore 60. Each of the above recesses may be machined by forming a circular bore from the interface 37, 39 or 41 with which it communicates prior to assembly of the sections 36, 38, 40 and 42.

Actuating means in the form of a solenoid 71 having a coil 72 and a plunger 74 are mounted in the section 42 for cooperation with the piston 62. The plunger 74 is dimensioned to have its axial travel limited by seating means 75 surrounding the plunger 74. The plunger 74 extends into a bore 76 formed in the section 42 coaxially disposed with the bore 62. Spring biasing means 80 are provided in a portion of the bore having a first end biased against the recess 65 and a second end against the radial flange 64. The plunger 62 is therefore normally disposed with the flange 64 in its forward position against the plunger 74.

The O-ring 68 preferably consists of ethylene propylene to provide for sealing, and plunger 62, in order to provide for inertness to reagents and low friction preferably consists of polytetrafluoroethylene (PTFE). The radial flange 64 connected to the plunger 62 preferably consists of aluminum. Of course, the plunger 74 of the solenoid 71 preferably consists of a steel rod for engaging the flange 64.

It is important that the dimensions of the above-recited components provide for accuracy in dispensing and for the limited amounts of dead volume described above. The length of axial travel in a transverse (forward to rear) direction of the piston 62 equals the depth or transverse dimension of the recess 70 minus the depth of the radial flange 64. The piston 62 is dimensioned for minimum clearance with the bore 60. The above-described stop means are preferably dimensioned such that at the limit of travel rearwardly, the rear end of the piston 62 is adjacent to but not at the rear surface of the bore 50. This prevents deformation of the rear surface of the piston 62 and eventual loss of precision in amounts of liquid dispensed.

In a nominal embodiment, in which it is desired to dispense exactly 500 microliters, the bore 50 is selected to have a diameter of 0.04 inches, the piston 62 has a diameter of 0.367 inches, and transverse travel of 0.288 inches is provided.

In operation, at desired times the solenoid 71 is pulsed by conventional control means (not shown) to cause the plunger 74 to move rearwardly. Consequently, the piston 62 is moved rearwardly as shown in the dotted line position in FIG. 2. Liquid in the pumping chamber defined by the portion of the bore 62 extending rearwardly of the rear end of the O-ring sealing means 68 and by the bore 50 is expelled through the outlet check valve 58. When the solenoid 71 is de-energized, the piston 62 returns to its normal position and reagent is aspirated into the pumping chamber through the inlet check valve 56.

Due to this construction, with the dimensions described above, a sufficient amount of reissue may be pumped while providing a 100 to 1 pumping ratio, i.e., the ratio between the amount pumped in one operating cycle and the volume of the pumping chamber when the piston 62 is in the actuated position. Consequently, at the initiating of operation of the analyzer, old reagent remaining in the pump is rinsed out in a minimum number of operating cycles. Cost of reagent which must be pumped is thus minimized. The reagent block assembly 22 provides the functions of a conduit assembly, providing a cylinder for the piston 62 and means for mounting the solenoid 71. Efficiency in operation and construction is thus provided.

What is claimed as new and desired to be secured by Letters Patent of the United States is:

1. In a chemical testing apparatus in which reaction containers are indexed through various positions, test samples and reagents ar dispensed into reaction tubes and the contents of the tubes are incubated and analyzed, the improvement of means for providing reagents for injection into the tubes comprising: a block assembly having a first bore extending therethrough and having forward and rear surfaces defining a reagent path therebetween, inlet and outlet means at respective opposite ends of said first bore for respectively communicating with a reagent source and a reagent dispensing line, a second bore communicating with said first bore at a forward surface of said first bore and extending forwardly thereof and defining a cylinder, a piston received in said cylinder, said piston having an end facing a rear surface of said first bore and being axially and reciprocally movable between a position in which said end is housed in said second bore and a position in which said piston extends into said first bore and said end is adjacent to said rear surface of said first bore, sealing means mounted coaxially with said second bore for surrounding said piston in said second bore, actuating means mounted to said block assembly for operating said piston, and stop means cooperating with said piston for limiting the travel of said piston in the transverse direction.

2. The improvement according to claim 1 wherein said sealing means is mounted in said second bore and defines a pumping chamber between said sealing means and said first bore.

3. The improvement according to claim 1 wherein said stop means comprises a radial flange connected to said piston, a chamber formed in said block assembly communicating with said second bore and having opposite axially disposed faces for engaging said radial flange.

4. The improvement according to claim 3 wherein said actuating means comprises a solenoid having a plunger, and wherein said plunger is mounted in said block assembly in axial registration with said piston in a further bore communicating with said second bore.

5. The improvement according to claim 4 wherein said block assembly is formed of a plurality of sections joined at transverse interfaces and wherein said recess comprises a bore extending transversely from one interface.

6. The improvement according to claim 5 further comprising first and second check valves mounted in said first bore on opposite sides of said second bore respectively.

7. The improvement according to claim 6 further comprising spring biasing means mounted in a recess coaxial with said second bore for biasing said piston toward said actuating means.

8. In a chemical testing apparatus in which reaction containers are indexed through various positions, test samples and reagents are dispensed into reaction tubes and the contents of the tubes are incubated and analyzed, the improvement of a reagent dispensing system comprising: a block assembly having a plurality of first bores extending therethrough, each first bore for providing a reagent path therethrough, a plurality of reagent supply bottles, a line for hydraulically coupling an inlet of each first bore to a reagent bottle, a reagent dispensing line hydraulically connected to an outlet of each first bore, a second bore disposed substantially normal to and opening into each first bore, each second bore defining a cylinder, a piston movable in each said cylinder and having means formed thereon for cooperating with stop means formed in a chamber communicating with each said second bore for limiting the axial travel of each piston, each piston being axially and reciprocally movable between a position within said second bore and a position in which an end of said piston extends out of said second bore into said first bore in the reagent path, and a plurality of actuating means, each mounted to said block assembly for actuating one piston.

9. The improvement according to claim 8 wherein each said stop means comprises a radial flange connected to one said piston and a chamber formed in said block assembly having transversely displaced faces each for engaging each said flange.

10. The improvement according to claim 9 wherein said actuating means each comprise a solenoid having a plunger in a bore in said block assembly, each said plunger being mounted coaxially with one piston.

* * * * *